Jan. 5, 1943. C. A. MARTIN Plant Pat. 564
APPLE TREE
Filed Dec. 2, 1941
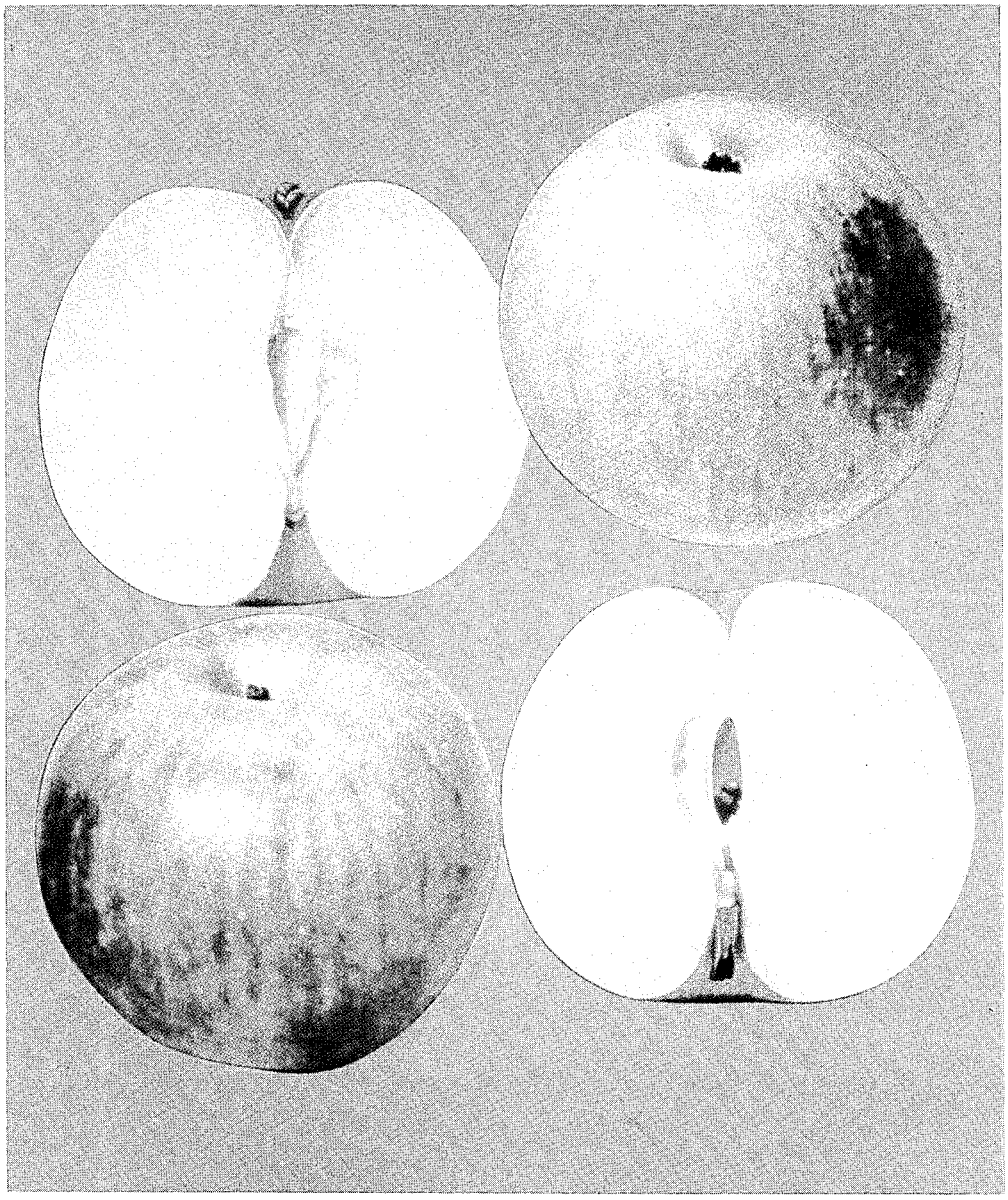
Inventor
C. A. Martin
By Robb & Robb
Attorneys Patented Jan. 5, 1943

Plant Pat. 564

UNITED STATES PATENT OFFICE

564

APPLE TREE

Charles A. Martin, Marthaville, La.

Application December 2, 1941, Serial No. 421,345

1 Claim. (Cl. 47—62)

The present invention or discovery relates to a new and distinct variety of apple tree, originating as a bud sport of a green variety growing in the deep South.

It is well known that applies do not do at all well in the section of Louisiana and other Southern States, so that any well colored fruit of good quality capable of growing in that territory where most standard varieties of apples are not suited, would possess great value, and this new variety appears to answer the desirable requirements.

The fruit possesses a much more attractive color than that of its parent as it is well known that red apples sell better on the market than other colored fruit, and, further, the new variety ripens, or is ready to eat, earlier than the parent variety. Other differences are found in the appearance of the foliage, being greener and more waxy, and in the shape of the fruit. There is no other variety indigenous to the South like it.

Observations show that the fruit of the new variety begins ripening about the 20th of July and continues to about August 10, whereas the parent variety ripens in August after that period.

The origin of this new variety is also unique. The parent tree is a green variety (name, if any, unknown), commonly found in central Louisiana. In late spring, after a wet season, when the parent tree showed much new growth, and while handling a limb, a twig of new growth and very sappy broke off. This was immediately placed in a hole at the root of the tree. Some time later, after this twig had taken root and grown a season or two, it was removed to a point some thirty feet away and allowed to develop normally. When it began to bear fruit, it was discovered to be unlike its parent in respect to the distinctions hereinbefore mentioned. Since the method of propagation referred to above is entirely unusual, or unsuccessful at least, in the Southern States of the country, this mutation to a superior apple, of distinct and desirable characters, holding true in asexual reproduction, is of great interest.

In the accompanying illustration is shown a specimen of the fruit in obverse positions and associated sections, as nearly as it is possible to depict the same.

The following is a detail description of the new variety, the color terminology being in accord with Ridgway's Color Standard and general dictionary meaning.

Specimens described were grown at Mora, county of Natchitoches, Louisiana.

Tree: Medium size; vigorous; upright, tall; vase-formed; rapid growing; hardy; productive; regular bearer.

Trunk: Medium stocky; smooth.

Branches: Thick; smooth; much branching; green.

*Lenticels.*—Medium number; medium large.

Leaves: Length—four inches; width—two and one-half inches. Medium large; medium wide; medium long; oval; abruptly pointed; thick; dark green; smooth.

*Margin.*—Coarsely serrate.

*Petiole.*—Length—one and one-half inches; medium long; thick.

Flowers: Dates of first and full bloom—April 9 and April 12; medium early; medium large; pink.

Fruit: Matures on or about August 15.

*Size.*—Variable; axial diameter—two and one-half inches. Transverse—two and three-fourths inches.

*Form.*—Globose; conical; ribbed faintly. *Cavity*—unsymmetrical; abrupt at base; acute; undulate. *Depth*—one-half inch. *Breadth*—three-fourths inch. *Markings*—russeting. *Basin*—unsymmetrical; rounded; undulate; pubescent; glabrous. *Depth*—five-eighths inch. *Breadth*—five-eighths inch.

*Stem.*—Medium slender; faintly pubescent. *Length* — one-half inch. *Breadth* — one-eighth inch.

*Calyx.*—Closed; persistent; lanceolate; acute. *Length*—three-sixteenth inch; erect; reflexed; outer surface and inner surface—pubescent.

*Eye.*—Medium size; partially closed.

*Skin.*—Thin; tough; smooth; rough; glossy; waxed. *Dots*—conspicuous; large; stellate. *Color of dots*—russet. *Distribution of dots*—thicker toward calyx end. *Ground color*—Baryta Yellow, Ridgway's Color Chart. *Color markings*—striped; splashed. *Color of markings*—Nopal Red stripes, Ridgway's Color Chart. *Bloom*—wanting. Scarskin—gray; distribution—light near cavity; general color effect—yellow ground nearly overspread with bright red stripes and splashes.

*Flesh.*—Juicy. *Color of flesh*—yellowish. *Texture*—firm yet tender; fine; crisp. *Flavor*—subacid; mild; aroma pronounced. *Quality*—very good.

*Core.*—Median. *Bundle area*—medium size; cordate; unsymmetrical at base. *Halves of area*—unequal. *Bundles*—green in two whorls. *Alternate bundle*—approximately to calyx tube; reaches tube above stamens. *Core line*—clasping, in cross section—distinct; carpellary area—distinct; large, open. *Calyx-tube*—glabrous toward base; funnel-form. *Stem of funnel*—short; depth of tube to shoulder—one-sixteenth inch. *Entire depth*—five-sixteenths inch. *Styles*—present; distinct toward base; pubescent. *Stamens*—in one distinct whorl; median. *Axillary cavity*—present. *Seed cells*—abaxile; very open. *Cell walls* — thin; tough. *Length* — seven-eighths inch; *breadth*—one-fourth inch. Longitudinal section narrowly ovate; mucronate. *Surface*—entire tufted.

*Seeds.*—Number perfect—one to three. Imperfect—none. Largest—three. Number in one cell—one; length—five-sixteenths inch; breadth—three-sixteenths inch. *Form.*—acute. *Color*—Seal Brown, Ridgway's Color Chart.

Use: Market; local; dessert; culinary.

Keeping quality: Medium.

Resistance to: Insects—good; diseases—medium.

I claim:

A new and distinct variety of apple tree, characterized as to novelty primarily by its early ripening period and red coloring of its fruit, substantially as shown and described.

CHARLES A. MARTIN.